United States Patent
Pessala et al.

(10) Patent No.: US 6,601,583 B2
(45) Date of Patent: Aug. 5, 2003

(54) VENTILATOR WHEREIN OPERATION IS MODIFIABLE DEPENDENT ON PATIENT SOUNDS

(75) Inventors: Tom Pessala, Ostersundom (FI); Mats Cardell, Solna (SE)

(73) Assignee: Siemens Elema AB, Solna (SE)

( * ) Notice: Subject to any disclaimer, the term of this patent is extended or adjusted under 35 U.S.C. 154(b) by 47 days.

(21) Appl. No.: 09/769,826

(22) Filed: Jan. 24, 2001

(65) Prior Publication Data

US 2001/0009153 A1 Jul. 26, 2001

(30) Foreign Application Priority Data

Jan. 25, 2000 (SE) .............................................. 0000205

(51) Int. Cl.[7] ............................................. A61M 16/00
(52) U.S. Cl. ............................. 128/204.23; 128/204.18
(58) Field of Search ...................... 128/204.18, 204.21, 128/204.23, 204.13, 204.14, 207.18, 205.23, 205.25; 600/529, 484, 534, 535

(56) References Cited

U.S. PATENT DOCUMENTS

| | | | | |
|---|---|---|---|---|
| 4,550,726 A | * | 11/1985 | McEwen | 128/202.22 |
| 5,092,326 A | * | 3/1992 | Winn et al. | 128/205.13 |
| 5,203,343 A | | 4/1993 | Axe et al. | |
| 5,245,995 A | * | 9/1993 | Sullivan et al. | 128/204.23 |
| 5,462,051 A | * | 10/1995 | Oka et al. | 600/300 |
| 5,836,302 A | * | 11/1998 | Homuth et al. | 128/205.23 |
| 5,857,458 A | * | 1/1999 | Tham et al. | 128/203.12 |
| 5,901,704 A | * | 5/1999 | Estes et al. | 128/204.21 |
| 5,947,115 A | * | 9/1999 | Lordo et al. | 128/200.24 |
| 5,953,713 A | * | 9/1999 | Behbehani et al. | 706/16 |
| 5,975,078 A | * | 11/1999 | Pauley | 128/205.23 |
| 6,062,216 A | * | 5/2000 | Corn | 128/204.23 |
| 6,116,241 A | * | 9/2000 | Huygen et al. | 128/204.23 |
| 6,164,277 A | * | 12/2000 | Merideth | 128/207.14 |
| 6,192,876 B1 | * | 2/2001 | Denyer et al. | 128/204.18 |
| 6,252,966 B1 | * | 6/2001 | Griffin | 381/70 |
| 6,273,088 B1 | * | 8/2001 | Hillsman | 128/204.18 |
| 6,287,264 B1 | * | 9/2001 | Hoffman | 600/529 |
| 6,290,654 B1 | * | 9/2001 | Karakasoglu | 600/529 |
| 6,342,040 B1 | * | 1/2002 | Starr et al. | 600/538 |
| 6,369,838 B1 | * | 4/2002 | Wallace et al. | 128/205.23 |
| 6,390,091 B1 | * | 5/2002 | Banner et al. | 128/202.22 |
| 6,398,739 B1 | * | 6/2002 | Sullivan et al. | 128/204.18 |
| 6,401,713 B1 | * | 6/2002 | Hill et al. | 128/204.18 |
| 6,431,171 B1 | * | 8/2002 | Burton | 128/204.18 |
| 2002/0104531 A1 | * | 8/2002 | Malone | 128/200.23 |
| 2002/0124848 A1 | * | 9/2002 | Sullivan et al. | 128/204.21 |
| 2002/0183642 A1 | * | 12/2002 | Murphy | 600/532 |
| 2002/0195105 A1 | * | 12/2002 | Blue et al. | 128/204.21 |

FOREIGN PATENT DOCUMENTS

| | | |
|---|---|---|
| DE | 197 50 536 | 5/1999 |
| WO | WO 98/50095 | 11/1998 |

OTHER PUBLICATIONS

"Speech Production During Mechanical Ventilation In Tracheostomized Individuals," Hoit et al, Journal Of Speech and Hearing Research, vol. 37, Feb. 1994, pp. 53–63.

* cited by examiner

Primary Examiner—Weilun Lo
Assistant Examiner—Teena Mitchell
(74) Attorney, Agent, or Firm—Schiff Hardin & Waite

(57) ABSTRACT

A ventilator for respiratory care, intended for connection to a patient, avoids needless alarms, caused by a patient's attempts to speak and needless suffering because of the patient's inability to trigger an alarm, by having a sound detector arranged to detect and identify sounds made by the patient, preferably intentionally. A control unit is operatively connected to the sound detector acts on at least one function in the ventilator on the basis of sounds identified by the sound detector.

15 Claims, 2 Drawing Sheets

VENTILATOR WHEREIN OPERATION IS MODIFIABLE DEPENDENT ON PATIENT SOUNDS

BACKGROUND OF THE INVENTION

1. Field of the Invention

The present invention is directed to a ventilator of the type having a tube adapted for communication with a patient's airways for exchanging gas with the patient in an inspiration phase and an expiration phase of a breathing cycle.

2. Description of the Prior Art

In respiratory care, particularly when a tracheal tube is used for connecting a patient to the ventilator, the patient sometimes finds it hard to communicate with others. Even if the patient succeeds in speaking some words, the ventilator often interprets this as a difference between the volume of inspired and expired breathing gas. This triggers an alarm that effectively drowns out any words spoken by the patient.

Corresponding problems can arise with ventilators with limited adaptability or inappropriate settings for the respiratory treatment. If the patient attempts to communicate the discomfort of struggling against the ventilator, this might not be noticed by anyone. When a staff member finally arrives (e.g. because a volume alarm is sounded), the patient may not be able to reveal her/his discomfort. No alarm might be triggered if the influence of the volumes is less pronounced.

Another problem exists with regard to patients who are conscious but too weak (or paralyzed) to be able to use the alarm button to attract the staff's attention. Therefore, these patients may experience pain or general discomfort without being able to summon help.

SUMMARY OF THE INVENTION

An object of the present invention is to provide a ventilator that solves the aforementioned problems, at least in part.

The above object is achieved in accordance with the principles of the present invention in a ventilator for respiratory care having a tube adapted for connection to a patient, and having a sound detector which detects and identifies sounds made by the patient, and a control unit operatively connected to the sound detector for influencing at least one function in the ventilator on the basis of sounds from the patient identified by the sound detector.

One or a number of new special functions can be added and performed by the ventilator with the use of a sound detector devised to detect sounds made by the patient, especially when the detected sounds can be interpreted as having been intentionally made by the patient.

Needless alarms (which would otherwise prevent the patient's voice from being heard) in particular can be inhibited and necessary alarms generated (e.g. summoning staff with an optical signal or some form of remote signal). The latter is especially advantageous when the patient makes unintentional sounds caused by e.g. pain.

Inhibition of alarms can be limited to certain types of discrepancies, e.g. a difference between inspired and expired volumes, and even limited to a certain sound magnitude, e.g. with specific upper and lower limits.

Other functions in the ventilator that could be affected on the basis of sounds from the patient are the volume of gas delivered in inspiratory phases (increase/decrease), the duration of inspiratory and expiratory phases (shorter/longer), changes in the respiratory mode (from controlled respiration to assisted respiration, from assisted respiration to spontaneous respiration or between different kinds of controlled, supported and spontaneous respiration).

DESCRIPTION OF THE PREFERRED EMBODIMENTS

Figure 1:
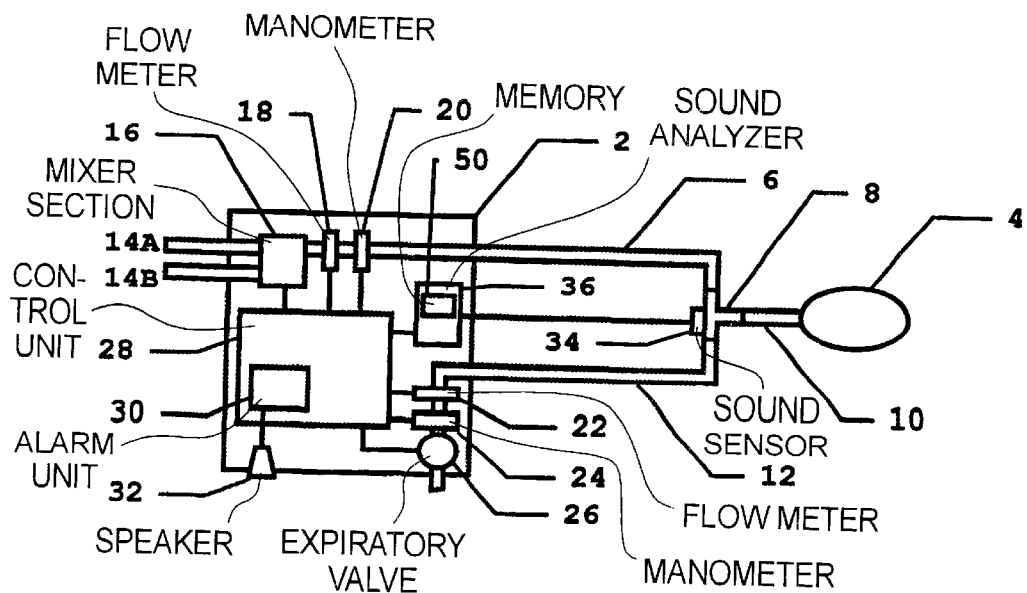
FIG. 1 shows a first embodiment of a ventilator according to the invention.

One embodiment of a ventilator 2 according to the invention is shown in FIG. 1. In this context, the term "ventilator" refers to all devices capable of providing respiratory assistance, i.e. respirators (high end and low end), resuscitators and anaesthetic machines are all regarded as ventilators in this context.

The ventilator 2 is connected to a patient 4 in order to provide some form of respiratory support. The ventilator 2 has an inspiratory line 6, a Y-piece 8, a tracheal tube 10 and an expiratory line 12. Other configurations for connecting components are possible.

A breathing gas can be prepared from gases delivered to the ventilator 2 through a first gas connection 14A and a second gas connection 14B. The gas is prepared in a mixer section 16 which contains e.g. valves etc. according to known prior art machines.

At the inspiratory side, the breathing gas passes a first flow meter 18 and a first manometer 20. These components can be integrated with the mixer section 16.

At the expiratory side, the breathing gas passes a second flow meter 22 and a second manometer 24 before the breathing gas is discharged through an expiratory valve 26.

All the functions in the ventilator are regulated by a control unit 28. The control unit 28 receives measurement signals from the available sensors and sends control signals to regulated components, e.g. in the mixer section 16. As known from prior art systems, the control unit 28 can include one or several processors, ROM, RAM, PROM, etc. the control unit 28 need further not be one single unit, but can be diversified into several smaller units with specialized functions.

The control unit 28 also includes an alarm unit 30. The alarm unit 30 can monitor a number of functions in the ventilator 2 and the patient 4. An alarm is generated when a fault occurs. An indication displayed on a screen (not shown in FIG. 1) is sufficient for some types of alarms, but an acoustic alarm should be sounded for most alarms. The alarm is sounded by a speaker 32.

The ventilator described thus far (with certain modifications) could be formed by virtually any known medical breathing apparatus.

A distinguishing feature of the ventilator according to the invention, which can be added to or designed into any known breathing apparatus, is a sound sensor 34 for detecting sounds and a sound analyzer 36 for identifying the voice of the patient 4 or sounds made by the patient 4 (preferably intentionally). The sound sensor 34 and the sound analyzer 36 jointly constitute a sound detector for detecting and identifying sounds.

The sound analyzer 36 is connected to the control unit 28 in order to perform sound analyses. The control unit 26 is modified to influence at least one function in the ventilator 2 based on the sounds made by the patient 4.

One possible function is for the sound analyzer's 36 identification of groans or corresponding sounds indicating that the patient is feeling pain or discomfort. The control unit 28 can then control the alarm unit 30 to generate an alarm for summoning staff.

The volume alarm is another alarm-related function that can be actuated. Most ventilators 2 monitor the volume of inspired and expired breathing gas. An alarm is generated when the discrepancy between these two volumes becomes excessive. This is because the cause may be leakage or some other defect requiring attention. However, the patient may be causing the discrepancy by expelling gas around the sides of the tracheal tube 10 to enable her/him to speak. No alarm is desirable in this situation, and if this fault arises at the same time as the patient speaks (as identified by the sound analyzer's 36), the control unit 28 can act on the alarm unit 30 to prevent the triggering of an alarm. Such an event should be logged (registered) to give the staff a better picture of the condition of the patient 4 and the operation and function of the ventilator 2.

In addition to inhibiting an alarm, the control unit 28 also can regulate the mixer section 16 and the expiratory valve 26 so gas flows during inspiration and expiration are adapted to (and facilitate) the attempts at speaking by the patient 4. Alternately, or as a complement, the control unit 28 can control the duration of inspiration and/or expiration.

Figure 2:
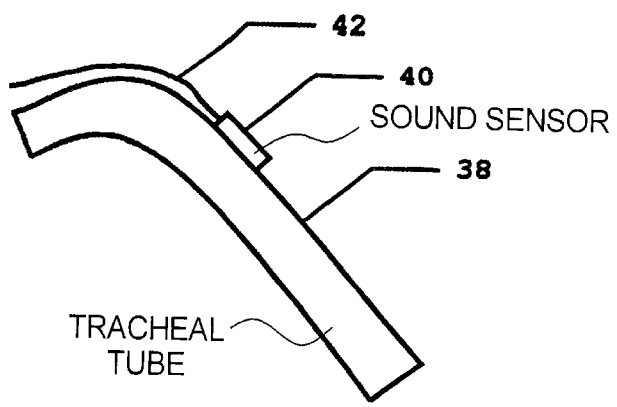
FIGS. 2 and 3 show alternative placements for a sensor means for detecting sound waves in the inventive ventilator.

The sound sensor 34 in the embodiment according to FIG. 1 is arranged near the patient 4 (on the exterior of the Y-piece 10). Other placements are possible. For example, FIG. 2 shows a tracheal tube 38 with a sound sensor 40 at the exterior thereof arranged and connectable by a signal line 42 to the sound analyzer 36.

Figure 3:
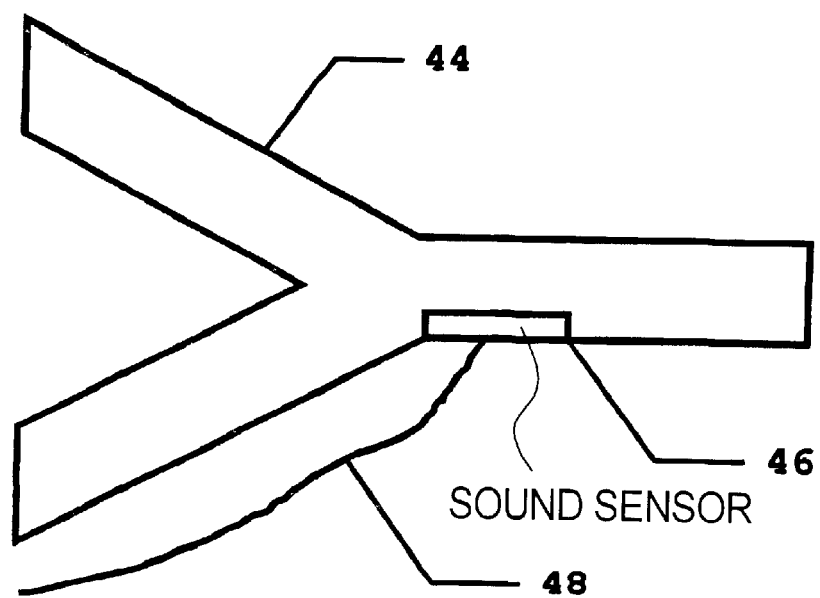

FIG. 3, which depicts a Y-piece 44, shows another example of an alternative location. A sound sensor 46 is arranged inside the Y piece 44 and is connected by a signal line 48 to the sound analyzer 36.

Other placements are immediately evident, such as on the patient (especially on her/his neck, near the vocal cords), etc.

The sound sensor can be a microphone, pressure-sensitive sensor, vibration-sensitive sensor or any kind of known sound-detecting sensor, depending on its placement.

As shown in FIG. 1, the sound analyzer 36 can be provided with a memory 50 to facilitate identification of sounds made by a patient 4. In an initial stage, samples of the voice of the patient 4 are stored in the memory 50. Sound subsequently detected by the sound sensor 34 can then be compared (spectrally or in some other way) to the stored sound. The sound analyzer 36 can advantageously include or be a frequency analyzer for analysis of the frequencies in the detected sound. Sounds from the patient 4 can then be identified from this analysis.

Although modifications and changes may be suggested by those skilled in the art, it is the intention of the inventors to embody within the patent warranted hereon all changes and modifications as reasonably and properly come within the scope of their contribution to the art.

We claim as our invention:

1. A ventilator comprising:
   a tube adapted for connection to a patient for providing respiratory care dependent on at least one of a plurality of ventilator functions;
   a sound detector for detecting and identifying sounds made by said patient;
   an alarm; and
   a control unit operatively connected to said sound detector for influencing at least one of said plurality of ventilator functions dependent on the sounds identified by said sound detector, said control unit being connected to said alarm and activating said alarm dependent solely on identification by said sound detector of sounds made by the patient.

2. A ventilator as claimed in claim 1 wherein said sound detector detects and identifies sounds intentionally made by said patient.

3. A ventilator as claimed in claim 1 wherein said sound detector includes a memory for storing recorded sound patterns from said patient, and wherein said sound detector subsequently compares detected sounds from said patient with the stored sound patterns to identify said detected sounds.

4. A ventilator as claimed in claim 1 wherein said sound detector includes a frequency analyzer for analyzing a frequency content of detected sounds to identify sounds made by said patient.

5. A ventilator as claimed in claim 1 wherein said sound detector includes a transducer for detecting sound waves selected from the group consisting of a microphone, a pressure sensor and an accelerometer.

6. A ventilator as claimed in claim 1 wherein said tube has a flow path therein for breathing gas, and wherein said sound detector is disposed in said flow path.

7. A ventilator as claimed in claim 1 wherein said respiratory care includes regulation of an inspiratory phase and an expiratory phase, and wherein said control unit, dependent on identification of said sounds by said sound detector, modifies said regulation of an inspiratory phase and an expiratory phase.

8. A ventilator comprising:
   a tube adapted for connection to a patient for providing respiratory care dependent on at least one of a plurality of ventilator functions;
   a sound detector for detecting and identifying sounds made by said patient;
   means for identifying a predetermined discrepancy between a volume of inspired breathing gas and a volume of expired breathing gas;
   an alarm; and
   a control unit operatively connected to said sound detector for influencing at least one of said plurality of ventilator functions dependent on the sounds identified by said sound detector said control unit being connected to said alarm and normally triggering said alarm if said predetermined discrepancy occurs, and said control unit inhibiting said alarm dependent on identification of sounds made by the patient by said sound detector.

9. A ventilator as claimed in claim 8 wherein said control unit inhibits said alarm for a limited period of time after identification of said sounds.

10. A ventilator as claimed in claim 8 wherein said sound detector detects and identifies sounds intentionally made by said patient.

11. A ventilator as claimed in claim 8 wherein said sound detector includes a memory for storing recorded sound patterns from said patient, and wherein said sound detector subsequently compares detected sounds from said patient with the stored sound patterns to identify said detected sounds.

12. A ventilator as claimed in claim 8 wherein said sound detector includes a frequency analyzer for analyzing a frequency content of detected sounds to identify sounds made by said patient.

13. A ventilator as claimed in claim 8 wherein said sound detector includes a transducer for detecting sound waves selected from the group consisting of a microphone, a pressure sensor and an accelerometer.

14. A ventilator as claimed in claim 8 wherein said tube has a flow path therein for breathing gas, and wherein said sound detector is disposed in said flow path.

15. A ventilator as claimed in claim 8 wherein said respiratory care includes regulation of an inspiratory phase and an expiratory phase, and wherein said control unit, dependent on identification of said sounds by said sound detector, modifies said regulation of an inspiratory phase and an expiratory phase.

* * * * *